United States Patent [19]
Fuller et al.

[11] Patent Number: 6,139,571
[45] Date of Patent: Oct. 31, 2000

[54] HEATED FLUID SURGICAL INSTRUMENT

[75] Inventors: Terry A. Fuller, Rydal; Aarne Reid, Meadowbrook, both of Pa.

[73] Assignee: Fuller Research Corporation, Rydal, Pa.

[21] Appl. No.: 08/890,053

[22] Filed: Jul. 9, 1997

[51] Int. Cl.$^7$ ................................................. A61F 7/00
[52] U.S. Cl. ................... 607/105; 607/113; 604/49; 604/113; 606/27; 606/31
[58] Field of Search .......................... 607/105, 113, 607/122, 138; 604/113, 114, 118, 49; 606/33, 49, 27, 32

[56] References Cited

U.S. PATENT DOCUMENTS

| | | | |
|---|---|---|---|
| 2,077,453 | 4/1937 | Albright | 128/254 |
| 2,192,768 | 3/1940 | Cross | 128/401 |
| 2,466,042 | 4/1949 | Reich et al. | 128/401 |
| 2,777,445 | 1/1957 | Hart | 128/303.12 |
| 3,369,549 | 2/1968 | Armao | 128/303.1 |
| 4,160,455 | 7/1979 | Law | 128/400 |
| 4,177,816 | 12/1979 | Torgeson | 128/400 |
| 4,646,737 | 3/1987 | Hussein et al. | 128/303.1 |
| 4,705,505 | 11/1987 | Fried | 604/80 |
| 4,949,718 | 8/1990 | Neuwirth et al. | 128/401 |
| 4,955,377 | 9/1990 | Lennox et al. | 128/401 |
| 5,159,925 | 11/1992 | Neuwirth et al. | 128/401 |
| 5,195,965 | 3/1993 | Shantha | 604/54 |
| 5,304,214 | 4/1994 | Deford et al. | 607/105 |
| 5,333,603 | 8/1994 | Schuman | 128/7 |
| 5,437,673 | 8/1995 | Baust et al. | 606/23 |
| 5,540,679 | 7/1996 | Fram et al. | 606/27 |
| 5,545,195 | 8/1996 | Lennox et al. | 607/105 |
| 5,607,420 | 3/1997 | Schuman | 606/15 |
| 5,891,094 | 4/1999 | Masterson et al. | 607/105 X |

OTHER PUBLICATIONS

Goldrath, M.H., Fuller, T.A., Segal, S. Laser Photovaporization of Endometrium For The Treatment of Menorrhagia, American Journal of Obstetrics and Gynecology 140:1 1981 p. 14–19.

Primary Examiner—Cary O'Connor
Assistant Examiner—Ryan Carter
Attorney, Agent, or Firm—Seidel, Canada, Lavorgna & Monaco, PC

[57] ABSTRACT

A heated fluid surgical instrument including a palm-sized handpiece having a cannula adapted to be inserted into a patient's body by way of a natural access (e.g., mouth) or a small incision. A channel is provided within the handpiece and the cannula for permitting the passage of a surgical accessory implement to the surgical site. Additional, channels are provided for passing fluid pumped into the handpiece from a remote fluid source to the surgical site. An irrigation control valve assembly on the handpiece permits a surgeon to selectively direct the flow of fluid through the handpiece and into one of two fluid flow paths. One of the paths heats the fluid and passes it to the surgical site to effect a therapeutic result. The other path sends the fluid directly to the surgical site.

16 Claims, 10 Drawing Sheets

HEATED FLUID SURGICAL INSTRUMENT

FIELD OF THE INVENTION

The present invention is directed to a surgical apparatus and method for delivering heated fluids to target tissue within a patient's body (e.g., to effect vasoconstriction, tissue coagulation, and tissue necrosis within body cavities, tissues, and organs).

BACKGROUND OF THE INVENTION

The medical profession has long recognized the therapeutic impact of heat applied to tissue within the body. It is known that heating tissue can alter its physical properties (e.g., thermal necrosis, thermal denaturation, coagulation, shrinkage, or vaporization). The therapeutic effect of heat ranges in temperature from approximately 37° C. (normothermic or body temperature) to hundreds of degrees Centigrade and depends on durations of exposure from fractions of a second to hours.

Not all tissue responds to temperature in the same way. For example, the temperature required to kill a malignant cell is known to be lower than that tolerated by most healthy cells. Thus, it is possible to use heat as a differential treatment for malignant disease. Similarly, localized elevated temperatures up to hundreds of degrees Centigrade can instantaneously destroy unwanted tissue, whether malignant or not.

Various surgical devices have been suggested to take advantage of the therapeutic effects of heat applied within the body. These include closed systems containing heated fluid circulated through expandable chambers or catheters adapted for placement proximate to or directly inside target tissue in a surgical site. However, these systems are subject to certain disadvantages and/or operating difficulties.

U.S. Pat. No. 5,545,195 (Lennox et al.) teaches a surgical instrument for interstitial heating of tissue. A sharp distal end of the instrument permits the instrument to be inserted into a solid mass within the body. An expandable chamber is then positioned in the insertion point and expanded within the tissue by the introduction of fluid into the chamber. A heating device located within the expandable chamber heats the fluid as the fluid fills the chamber. A disadvantage of this instrument (for which there is no teaching of the required temperature or clinical end-point for it to be effective) is that the size and shape of the expandable chamber itself impedes the application of heat to difficult to reach anatomic areas. Another serious disadvantage of this instrument is that it must be inserted into the tissue mass. This can be difficult to accomplish depending upon the type of tissue, its anatomic location, vascularity, etc. If the mass can be reached, the sharp distal end may cause bleeding which can obscure the surgeon's view of the surgical site. In addition, the expansion of the chamber within the mass may cause ripping or tearing of tissue. In the worst case, trauma caused by the insertion of the instrument may bring about the spread of malignant cells from the solid mass. The sharp distal end may also inadvertently cause damage to tissue in sites other than the surgical site—a serious concern in endoscopic procedures. Indeed, in certain cases, use of sharp instruments are contraindicated due to the risk of puncturing vital structures.

Other devices employing heated fluids contained in expandable chambers or catheters include the devices disclosed in U.S. Pat. No. 4,949,718 (Neuwirth) for treatment of uterine endometrium; U.S. Pat. No. 4,955,377 (Lennox et al.) for use within blood vessels during balloon angioplasty; U.S. Pat. No. 5,195,965 (Shantha) for treatment of viral infections and cancers; and U.S. Pat. No. 5,540,679 (Fram et al.) for ablation of conduction pathways in the heart. These devices, however, are subject to some or all of the disadvantages described above. Furthermore, no indications are given in the above-identified references regarding the required temperatures or clinical end-point for these devices to be effective.

U.S. Pat. No. 4,160,455 (Law et al.) teaches incorporating a heating element within a container or catheter positioned inside a body cavity. A pump causes fluid to be drawn from the body cavity into the container holding the heating element. At least some of the fluid is heated and expelled into the body cavity. A serious disadvantage of this device (for which there is no teaching of the required temperature or clinical end-point for it to be effective) resides in the heating element being introduced into the body cavity within the cylindrical container at the distal end of the device. Because the container houses the heating element, multiple thermistors, and other elements required to provide heated fluid, the cylindrical container is larger than the connecting pipe. The size of the container limits its ability to access tissue within the body. After insertion into the body, the container may inadvertently and undesirably contact adjacent tissue. The size of the container also limits the volume of fluid to be heated and the flow rate of fluid expelled. Furthermore, using heated body fluid gives rise to the added limitation of fouling the heater with coagulated proteins and the like.

In the medical arts, the application of warmed fluid directly on tissue (rather than in a closed container placed against the tissue) has historically been limited to bathing the integument at temperatures generally below 50° C. The use of hotter fluid has been limited to surgical procedures where filling an entire anatomical site with fluid having a temperature in excess of 50° C. would not cause excessive harm. For example, super-heated water and steam have been applied in the uterus in the treatment of uterine bleeding. This treatment has been abandoned by the medical profession largely because of the problem of uncontrolled burning. Electro-surgical treatments, laser surgical treatments, and, to a large degree, treatments employing heated fluid in closed systems have since replaced this treatment. However, as with the treatments involving contained heated fluid, electro-surgery and laser surgery are not free from disadvantages.

High-frequency current from an electro-surgical unit (ESU), is widely used to cut tissue and coagulate bleeding vessels. Heat is generated by conduction of the electrical current through the tissue. Tissue temperature during electro-surgery can be as high as 800° C. to 1000° C. A limitation of the ESU is that the electrical current may travel through paths of least resistance to damage vital structures which are not the focus of the surgical procedure. Additionally, the current may stimulate nerves and muscles resulting in unwanted twitching or movement of tissue during surgery. These hazards limit the use of the ESU with respect to applications near vital structures. For example, surgeons are generally loathe to use the ESU for surgical procedures within the nasal sinus, particularly near the eye or at the base of the skull. Another limitation is arcing between an ESU electrode and surrounding tissue. Arcing perforates tissue. Thus, use of an ESU for lung surgery is contraindicated.

Lasers are commonly-employed devices for elevating tissue temperature. Absorption of optical radiation by tissue causes the tissue temperature to rise. When delivered appropriately, tissue temperatures may be increased from a few degrees, for shrinkage of collagen for example, to 800° C. to 1200° C. for incisional surgery or wide area ablation. Unfortunately, lasers and the requisite fiber optic delivery devices are very expensive and difficult to use. They often have special power and water requirements. They require special training in their use. They also require the implementation of special safety devices and measures (e.g., protective eye wear, signs on operating theater doors warning prospective entrants of the presence of laser light). Furthermore, like the ESU and the known heated fluid devices, lasers require additional specially-trained operating personnel (i.e., nurses, technicians, or other medical assistants) to adjust the device intraoperatively. Beyond these economic and convenience issues, lasers have other limitations. For example, lasers that operate at a wavelength appropriate to heat target tissue may also operate at a wavelength that scatters energy into non-target anatomical structures causing harm thereto. Another limitation is that beam duration must be monitored with the utmost care. If the laser is not shut off immediately after vaporizing the target tissue, the beam will continue in a straight line, vaporizing or coagulating healthy tissue. This hazard is particularly acute when operating on tissue overlying vital anatomical structures.

Lasers have been used in conjunction with probes that contact tissue. Infrared absorbing materials have been placed on the distal end of a fiber optic device to concentrate the power density toward the end of the contact element and to convert some or all the optical energy into heat. The heat, either alone or in combination with the light, affects the tissue. The combination of heat and laser radiation is used in the treatment of soft tissue in and around the oral and nasal cavities. Contact laser approaches are limited by the same economic and convenience issues as described above in connection with conventional lasers. In addition, the delivery systems used for this type of surgery are quite fragile and are easily damaged. Probe damage is a serious concern, as high power optical energy is often being surgically applied around the eye and brain.

There is a need, therefore, for a surgical instrument suitable for endoscopic applications that, in the hands of a surgeon, is capable of precisely and safely delivering a controlled flow of heated fluid directly to target tissue in the surgical site, and that is free from the disadvantages and adverse effects associated with the known surgical devices identified above.

SUMMARY OF THE INVENTION

The present invention is directed to a heated fluid surgical instrument and method that satisfies the above-identified need. The heated fluid surgical instrument as contemplated by the present invention includes a palm-sized handpiece including a rigid or flexible cannula operatively connected thereto. The cannula is adapted to be inserted into a patient's body by way of a natural access (e.g., the nose, mouth, or rectum) or by a small incision in the body (e.g., into anatomical locations such as the pleural cavity, abdomen, or neck). A channel is provided within the handpiece and the cannula for permitting the passage of a surgical accessory implement (such as a cutting tool, a telescope, a manipulator, a secondary aspiration and irrigation device, etc.) into the surgical site. Additionally, channels within the handpiece and cannula are provided for passing fluid pumped into the handpiece from a remote fluid source ultimately into the surgical site. An irrigation control valve assembly operatively associated with the handpiece permits a surgeon/ operator to selectively direct the flow of the fluid through the handpiece and into at least one of a first and a second fluid flow path. The first fluid flow path bypasses a hot fluid reservoir defined within the handpiece and passes the fluid through the handpiece, into and through the cannula, and out the distal end of the cannula into the surgical site to irrigate the surgical site. The second fluid flow path passes the fluid through the hot fluid reservoir where the fluid is heated to a controlled preselected temperature by a heater disposed in the handpiece. The heater is selectably powered by a temperature controller which receives fluid temperature information sensed by one or more temperature sensors disposed in the handpiece and/or in the cannula. The heated fluid from the hot fluid reservoir is passed into and through the cannula and out the distal end of the cannula into the surgical site to effect a therapeutic result. The selected position of the irrigation valve assembly also controls the average flow rate of fluid exiting the cannula, the mix of first and second fluid flows, and the average fluid temperature.

In an alternative embodiment of the present invention, the handpiece is provided with an aspiration valve assembly in addition to the irrigation control valve assembly. The aspiration valve assembly is operatively connected to a remote suction device via suction tubing. The device exerts negative pressure through the tubing and the aspiration valve assembly. The aspiration valve assembly permits the surgeon/ operator to control the suction pressure to effect the withdrawal of fluid or friable tissue from the surgical site.

In another embodiment of the present invention, the distal end of the cannula is optionally fitted with one of a set of interchangeable tissue contact tip assemblies each including a tissue contact tip for facilitating the flow of hot fluid to the target tissue and for providing tactile feedback upon contact with the tissue. The tissue contact tip assembly may employ tissue contact tips of various geometries including a roller ball tip, a flat tip, an orbital tip, and a perforated tip. Additionally, the tissue contact tip assembly may be adapted to function as a valve to control the flow of heated fluid exiting the cannula upon contact with tissue in the surgical site. The tissue contact tip assembly may also be adapted to permit exertion of a constant compression force on tissue.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 6b is a graphical illustration of a temperature gradient associated with the surgical instrument of FIG. 6a.

FIG. 8b is a cross-sectional view of the alternative tissue contact tip assembly of FIG. 8a.

DESCRIPTION OF THE INVENTION

Figure 1:
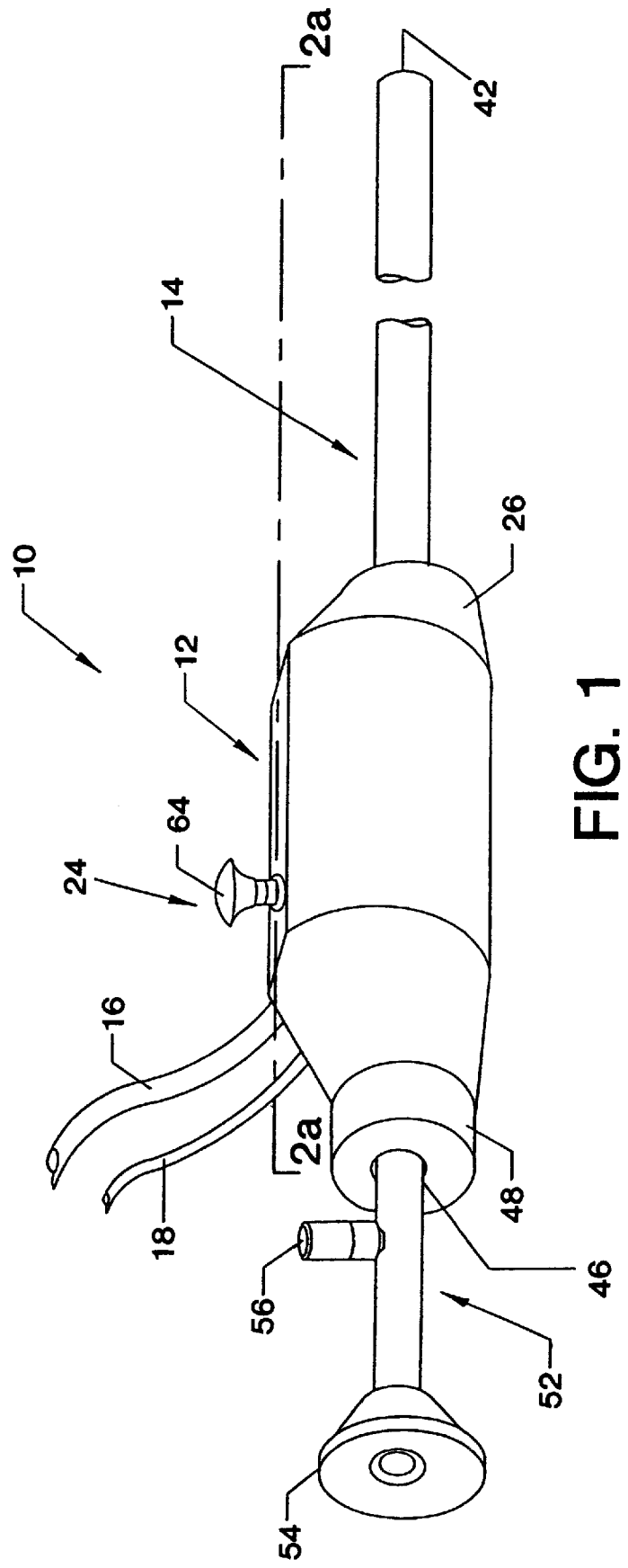
FIG. 1 is an isometric view of a heated fluid surgical instrument according to the present invention.

Referring now to the drawings, wherein like reference numerals indicate like elements, there is shown in FIG. 1 a heated fluid surgical instrument 10 in accordance with the present invention. The instrument 10 includes a handpiece 12 and a cannula 14 removably attached thereto and extending therefrom. An input fluid tube 16 originating from an irrigation fluid source is removably attached and fluidly sealed to the handpiece 12. The tube 16 is provided to carry a physiologically compatible irrigation fluid such as saline, dextran, water, intravenous fluid, or the like into the handpiece 12. A heater power line 18 is provided to bring electrical power from a temperature controller 20 (shown in FIG. 5) to a heater 22 (shown in FIG. 2a) housed in the handpiece 12 for raising the temperature of the irrigation fluid. An irrigation control valve assembly 24 associated with the handpiece 12 enables the surgeon or operator to control both the flow and temperature of the irrigation fluid through the handpiece and cannula 14 as described in greater detail hereafter.

Figure 2A:
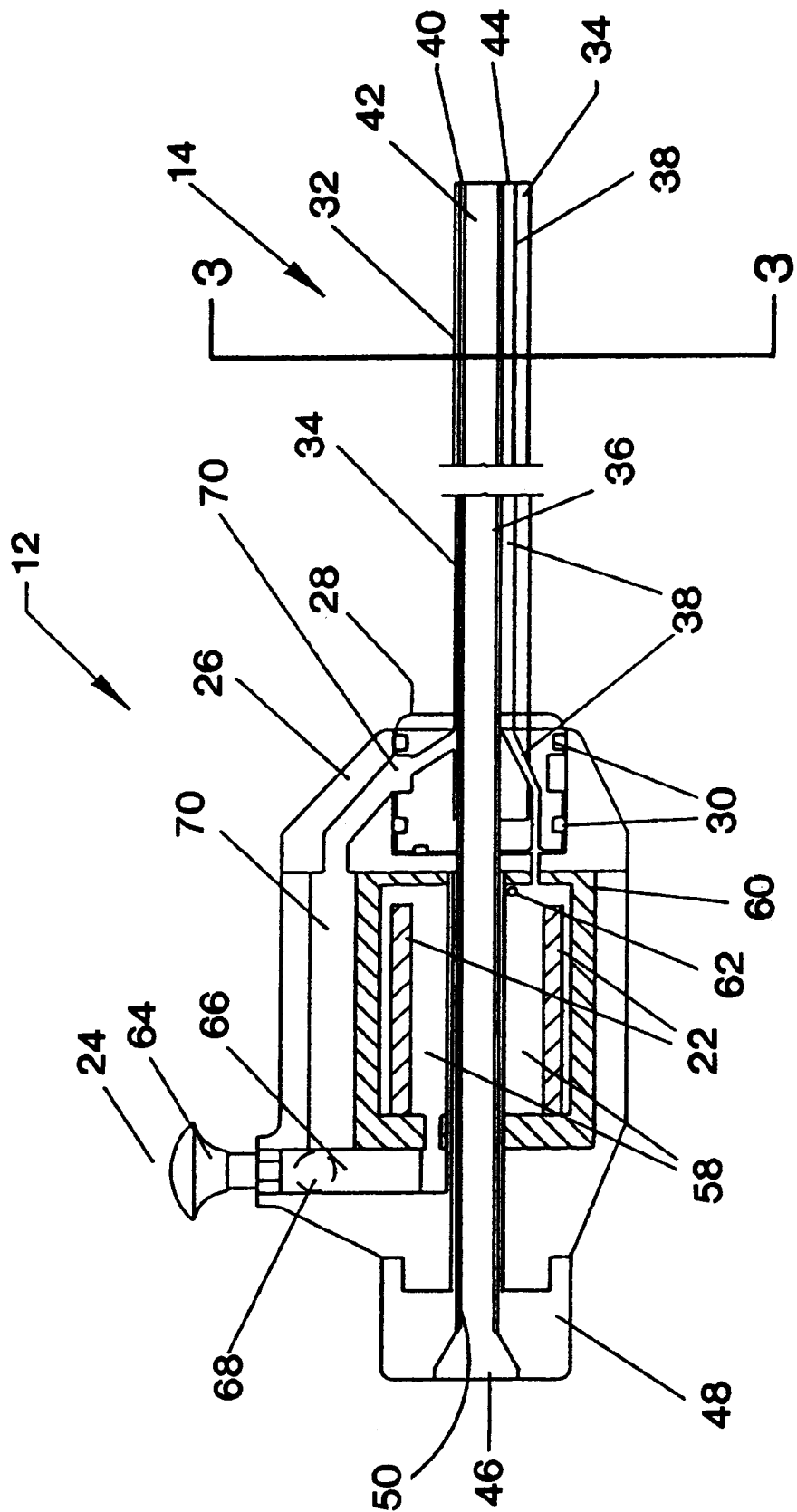
FIG. 2a is a longitudinal cross-sectional view of the surgical instrument taken along line 2a—2a in FIG. 1.

Referring to FIG. 2a, the cannula 14 is removably connected to the handpiece 12 at a handpiece nose portion 26 by a cannula interface 28 and sealed with a seal 30. It should be appreciated that the seal 30 may be any suitable type of seal mechanism including an O-ring seal. Indeed, the interface 28 itself could be the seal mechanism.

Figure 3:
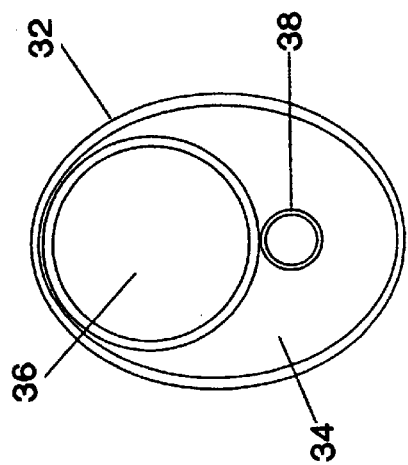
FIG. 3 is a transverse cross-sectional view of a cannula assembly of the surgical instrument taken along line 3—3 in FIG. 2.

An outer sleeve 32 of the cannula 14 surrounds an irrigation channel 34, an accessory channel 36, and a hot fluid channel 38. FIG. 3 is a transverse cross-sectional view of the cannula 14 taken along line 3—3 in FIG. 2a showing this arrangement. The irrigation channel 34, the accessory channel 36, and the hot fluid channel 38 terminate at the distal end of the cannula 14 at an irrigation port 40, an accessory exit port 42, and a hot fluid port 44, respectively.

It should be understood that the cannula 14 may be of any suitable length or dimension. Additionally, the cannula 14 may be formed of a rigid or a flexible material having a durability sufficient for either a single use or for multiple re-uses.

The handpiece 12, which is preferably sized to fit comfortably in the hand of the surgeon/operator, includes an accessory entry port 46 preferably provided in an adjustable connecting ring 48. The entry port 46 is adapted to accept at least one of a set of surgical accessories such as a telescope, a cutting instrument, or other device for introduction into the surgical field by way of an accessory tube 50 which extends through the handpiece 12 and connects to the accessory channel 36 in the cannula 14 (which terminates at the accessory exit port 42 at the distal end of the cannula). The selection and configuration of surgical accessory instruments is well within the knowledge of those skilled in the medical arts. Desirably, the cannula 14 and surgical accessories placed in the accessory entry port 46 are capable of being rotated relative to and independently of each other and of the handpiece 12.

FIG. 1 shows a conventional surgical telescope 52 inserted through the entry port 46 for introduction into the surgical site by way of the exit port 42 to enable the surgeon/operator to visualize the tissue under treatment. The telescope 52 contains an eyepiece 54 and a light source connector 56.

Figure 4:
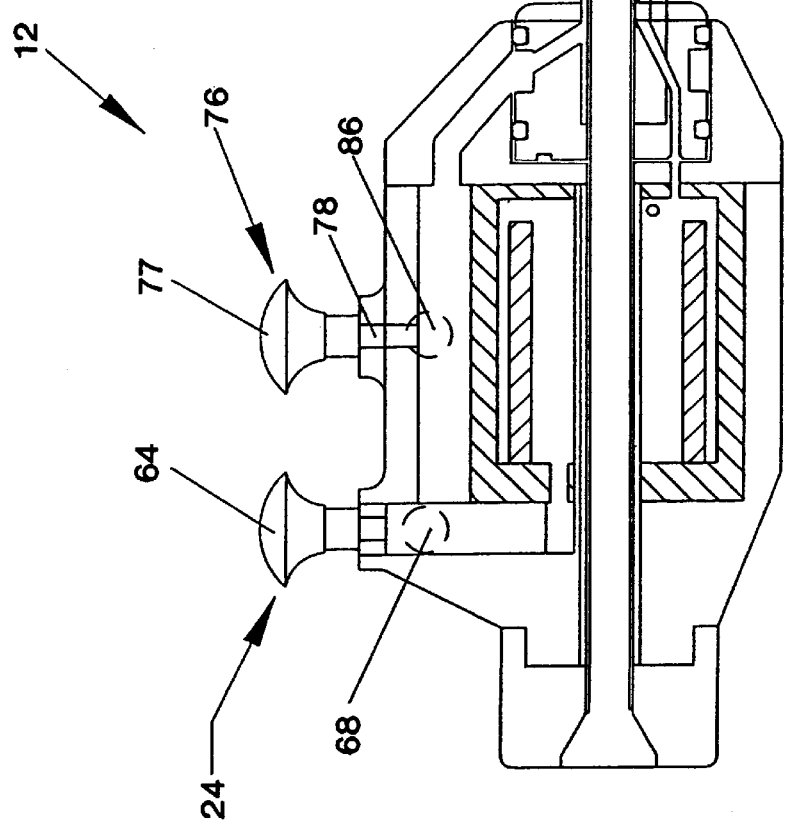
FIG. 4 is a longitudinal cross-sectional view of an alternative embodiment of the surgical instrument.

Referring to FIG. 2a, the handpiece 12 houses the heater 22 which is preferably disposed in or surrounding a hot fluid reservoir 58 defined within the handpiece. The heater 22 may be of any suitable design. Preferably, the hot fluid reservoir 58 and the heater are insulated by insulation—desirably, a thin vacuum insulation shell 60 (FIGS. 2a and 4).

The location of the heater 22 is an important feature of the present invention. The invention places the heater 22 within the handpiece 12. This is close to the target tissue and in a non-obtrusive location. It should be appreciated that placement of the heater 22 within the handpiece 12 avoids certain disadvantages associated with prior art instruments that use fluid heated at the fluid source. Specifically, it avoids the problem of the fluid cooling to unacceptable levels (i.e., in the long tubes emanating from the heated fluid source) before it ultimately reaches the surgical site. The location of the heater 22 also eliminates the need to thermally insulate the long tubes. Insulated tubes are heavy and cumbersome. Importantly, with the present invention, the distal end of the fluid delivery cannula can be very small and anatomically correct in its shape, unlike the fluid filled balloons known in the art.

The temperature controller 20 (shown in FIG. 5) supplies power to the heater 22 (via power line 18) sufficient to maintain a preset (i.e., by the surgeon/operator) hot fluid temperature in response to inputs received from at least one temperature sensor 62 (e.g., a thermocouple or a temperature transducer). The sensor 62 (FIGS. 2a and 4) may be positioned proximate the hot fluid channel 38 within the handpiece 12 or distal to it (e.g., within the cannula 14). The temperature controller 20 and the temperature sensor 62 may be any appropriate combination of available devices, but are preferably a PID (proportional integral derivative) controller and an RTD (resistance temperature detector) transducer.

Figure 2B:
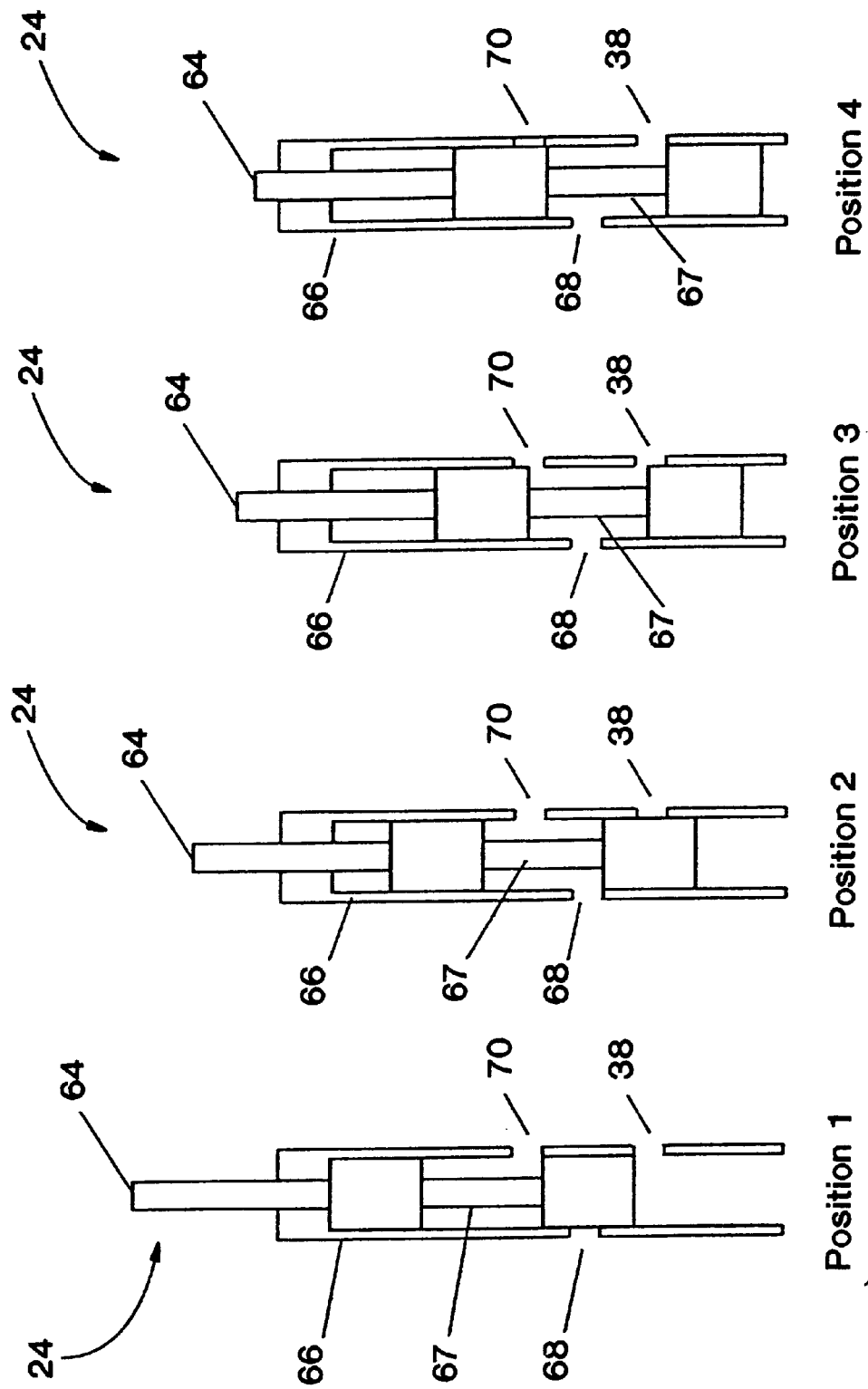
FIG. 2b is a series of cross-sectional views illustrating the various operational positions of an irrigation valve assembly of the surgical instrument according to the present invention.

The handpiece 12 also houses the irrigation control valve assembly 24 which controls the flow of fluid through the handpiece (as described in greater detail hereafter). Desirably, the valve assembly 24 is a trumpet valve (best shown in FIGS. 1, 2a, and 10) including an operator interface control (button) 64 and an associated irrigation valve body 66 and valve stem 67 (FIG. 2b). An irrigation fluid conduit 68 connects the irrigation valve body 66 to the input fluid tube 16.

The hot fluid channel 38 runs from the hot fluid reservoir 58 defined in the handpiece 12 into and through the cannula 14. An irrigation channel 70 also defined within the handpiece 12 extends from the valve body 66 into and through the outer sleeve 32 of the cannula 14. The irrigation channel 70 provides a connection between the valve body 66 and the outer sleeve 32 depending upon the selected position of the valve body.

Figure 5:
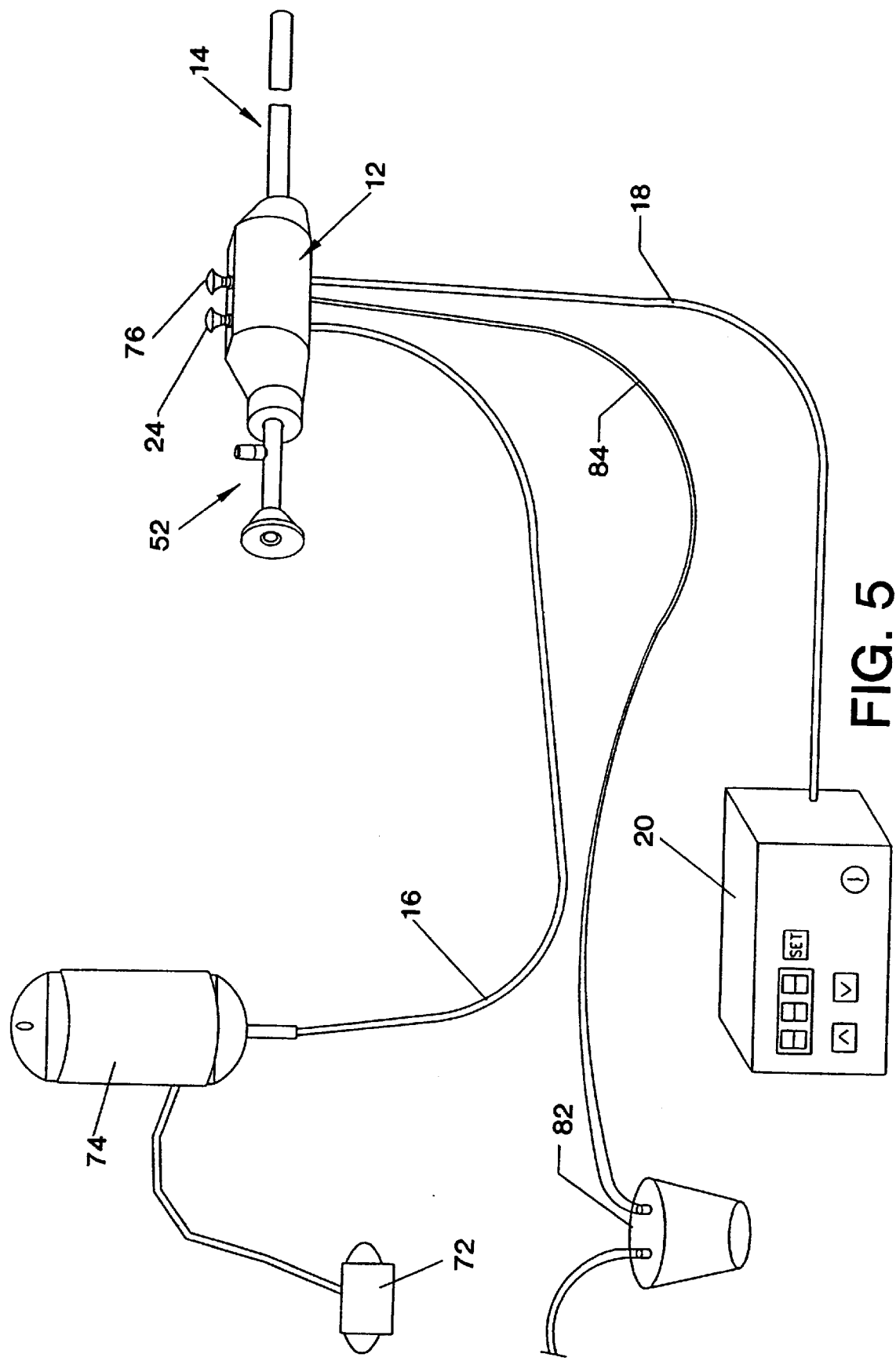
FIG. 5 is a system schematic showing the surgical instrument of FIG. 4 and support instrumentation.

In operation, irrigation fluid is delivered under pressure from an irrigation fluid source, through the input fluid tube 16, and into the irrigation valve body 66 in the handpiece 12 via the irrigation fluid conduit 68. It should be understood that the irrigation fluid may be forced through the input fluid tube 16 by any suitable means, including by an air pressure pump 72 operatively connected to a pressure cuff 74 disposed about a fluid bag 75 (as shown in FIG. 5 in connection with an alternative embodiment of the invention).

Depending upon the position of the valve stem 67 in the valve body 66 of the irrigation control valve assembly 24, the fluid may take a first flow path into and through the irrigation channel 70 within the handpiece 12, past the handpiece nose 26, and into and through the outer sleeve 32 of the cannula 14 to exit the irrigation port 40 at the distal end of the cannula. With this configuration, the temperature of the irrigation fluid exiting the cannula 14 is substantially the same as or less than the temperature at which it was delivered to the handpiece 12.

The irrigation fluid may also take a second flow path. The flow may be directed by the irrigation control valve assembly 24 into the hot fluid reservoir 58 where the irrigation fluid is heated by the heater 22 to a predetermined therapeutic temperature required for the procedure. In operation, the fluid heated within the hot fluid reservoir 58 flows past the handpiece nose 26, through the hot fluid channel 38, and exits the hot fluid port 44 at the distal end of the cannula 14. Preferably, the temperature of the irrigation fluid exiting the cannula 14 in this configuration will range from normothermic (i.e., body temperature) to a temperature that may exceed 150° C., depending on the maximum desired temperature set by the surgeon (i.e., via the temperature controller 20).

The irrigation control valve assembly 24 controls the flow of the irrigation fluid exiting the cannula 14 (preferably in a continuous manner) as described in the following truth table and as illustrated in FIG. 2b:

| Irrigation valve assembly 24 position | Fluid from irrigation channel 70 | Fluid from hot fluid channel 38 |
| --- | --- | --- |
| 1 | off | off |
| 2 | on | off |
| 3 | on | on |
| 4 | off | on |

Desirably, the flow rate of the irrigation fluid exiting the cannula 14 may be adjusted to range up to approximately 500 ml/min. The flow rate of the heated fluid (i.e., the second fluid flow) is preferably less than that of the unheated fluid (i.e., the first fluid flow) to permit accurate and controlled application of heat to target tissue in the surgical site.

In a preferred embodiment (best shown in FIGS. 4 and 5), the handpiece 12 includes an aspiration valve assembly 76 in addition to the irrigation valve assembly 24. Desirably, the aspiration valve assembly 76 is a trumpet valve including an operator interface suction control (button) 77 and an associated suction valve 78. Adjustment of the aspiration valve assembly 76 permits control of aspiration from an irrigation/aspiration channel 80 within the cannula 14 and from the surgical site. Suction pressure from a suction device 82 is exerted through an aspiration fluid tube 84 and through an aspiration fluid conduit 86 in the handpiece 12 which connects the aspiration fluid tube to the suction valve 78 of the aspiration valve assembly 76. The suction valve 78, which controls the suction, may be biased in a closed position and the suction control 77 may be biased such that the surgeon must continuously depress the control to provide the desired degree of suction from the surgical field.

In combination, the irrigation valve assembly 24 and the aspiration valve assembly 76 may be used to precisely control the temperature of the fluid reaching the tissue, ranging from the temperature of the irrigation source to the maximum set temperature, as well as the flow rate, adjusted and proportional to the settings of the valve assemblies. Although the valve assemblies 24 and 76 have been described as mechanical valves, it should be understood that non-mechanical valves which can be controlled by the surgeon/operator (e.g., servo valves) may be employed.

In all configurations of the present invention a controlled temperature gradient is generated in the tissue as a result of the fluid flow. In the embodiment employing both irrigation and aspiration valve assemblies 24 and 76, the aspiration valve assembly changes the direction of flow in the irrigation/aspiration channel 80 and adjusts the degree of aspiration proportional to the valve setting. With this combination of irrigation flow and aspiration a broad range of temperature gradients can be obtained. It should be appreciated that the temperature gradients or profiles created by use of the present invention will vary depending upon the type of fluid used, the flow rates, anatomy, and other factors.

Figure 6A:
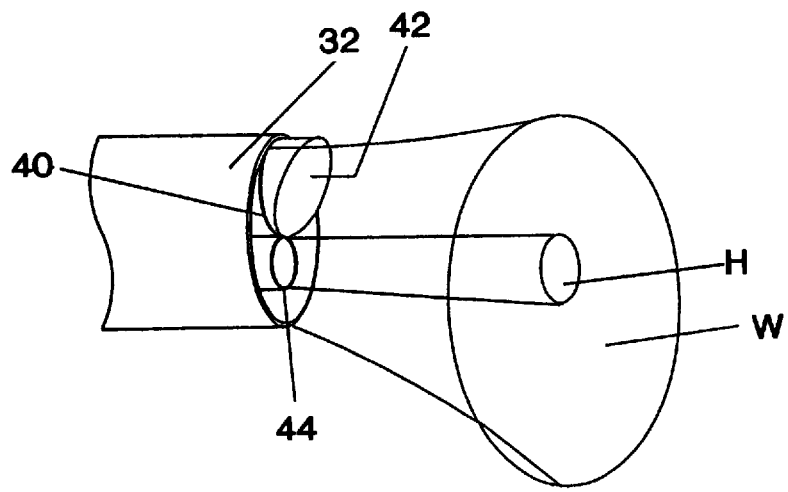
FIG. 6a is an enlarged view of the distal end of a cannula of one embodiment of the heated fluid surgical instrument illustrating the fluid paths exiting therefrom.
Figure 6B:
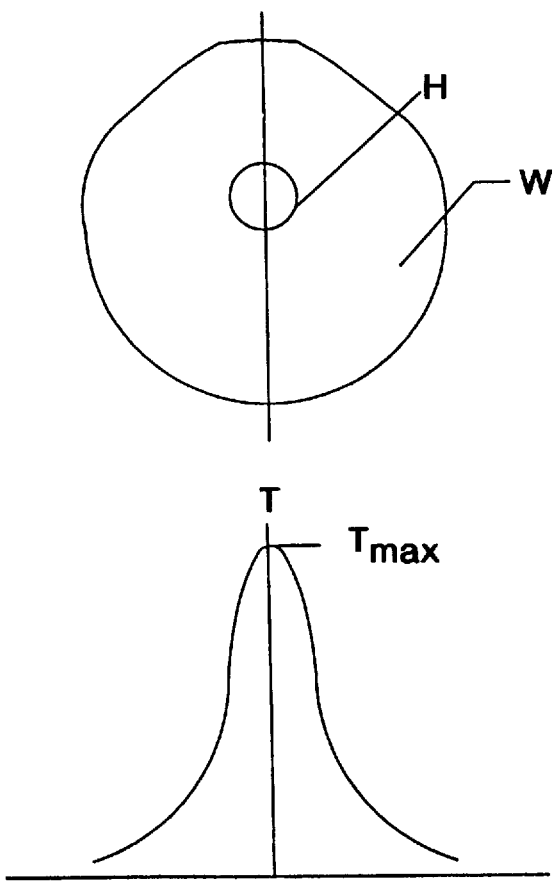

As shown in FIGS. 6a and 6b heated fluid H exits the hot fluid port 44 and, depending upon the position of the irrigation valve assembly 24, is surrounded with secondary fluid W from the irrigation/aspiration channel 80. The mixing of the fluids is a function of the flow rates of the fluids W and H as well as the location and geometry of the target tissue. Generally, a steep temperature gradient (FIG. 6b) resulting from the temperature of heated fluid H is achieved (the temperature gradient associated with a heated fluid surgical instrument fitted with a tissue contact tip assembly, discussed hereafter, may be steeper depending upon the set temperature).

In practice, the following typical average hot "H" and secondary "W" fluid flow rates and configuration have been found to be suitable:

| Disorder | Max H temp. | H flow | H temp. | W Flow | Configuration* |
| --- | --- | --- | --- | --- | --- |
| ENT | | | | | |
| Nasal Polyp | 60–80° C. | 30 ml/mn | 39–41° C. | 350 ml/mn | NCT or CT |
| Turbinectomy | 70–85° C. | 30 ml/mn | 39–41° C. | 350 ml/m | CT |
| Head and neck cancer resection | 80–150° C. | 70 ml/mn | 39–41° C. | 100 ml/m | CT |

-continued

| Disorder | Max H temp. | H flow | H temp. | W Flow | Configuration* |
|---|---|---|---|---|---|
| Thoracic | | | | | |
| Diffuse bullae | 70–85° C. | 5 ml/m | 20–40° C. | 20 ml/m | NCT or CT |
| Lung reduction | 70–85° C. | 5 ml/m | 20–40° C. | 20 ml/m | NCT or CT |
| Adhesiolysis | 80–120° C. | 10 ml/m | 20–40° C. | 30 ml/m | CT |
| GI/GS | | | | | |
| Barrett Esophagus | 60–75° C. | 30 ml/m | 25–40° C. | 100 ml/m | NCT |
| Vascula GI disorders | 55–75° C. | 150 ml/m | 39–41° C. | 150 ml/m | NCT |
| GYN | | | | | |
| Uterine Menorrhagia | 80–90° C. | 150 ml/m | 39–41° C. | 350 ml/m | NCT or CT |
| Endometriosis | 80–90° C. | 20 ml/m | 20–40° C. | 50 ml/m | CT |

*Note:
"CT" = contact tip; "NCT" = no contact tip. Where "NCT or CT" configurations are given, H flow equals the flow rate for the NCT configuration.

Figure 7D:
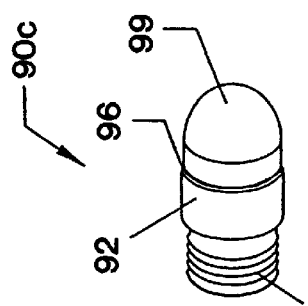
FIG. 7a is an enlarged view of the distal end of a cannula of one embodiment of the heated fluid surgical instrument fitted with a tissue contact tip assembly.
FIGS. 7b,c,d,e are isometric views of various interchangeable tissue contact tips.
Figure 7E:
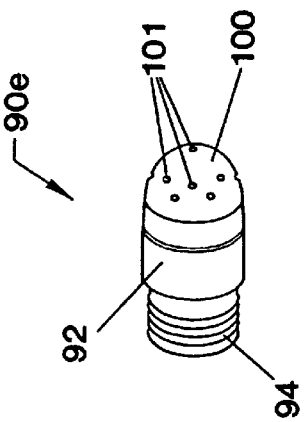
Figure 7B:
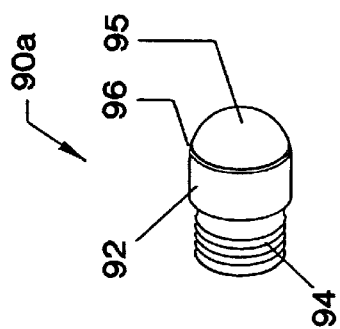
Figure 7C:
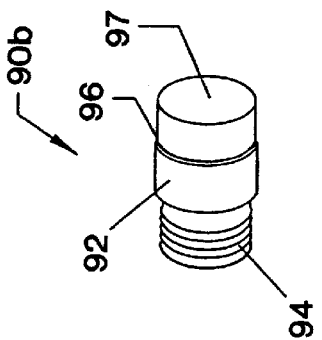
Figure 7A:
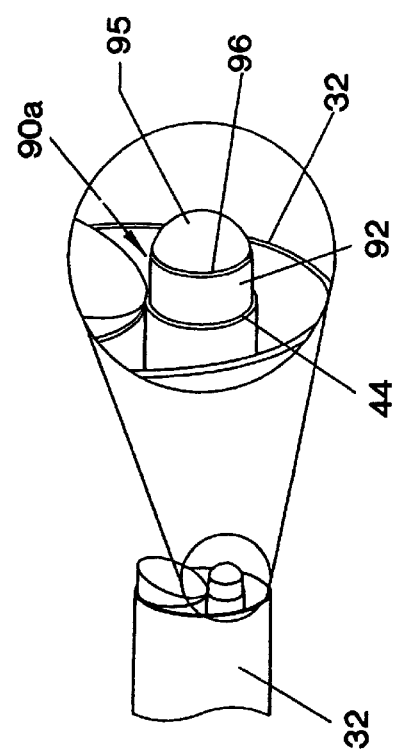

FIG. 7a illustrates an alternative embodiment of the present invention whereby the hot fluid port 44 of the distal end of the cannula 14 is fitted with one of a set of interchangeable tissue contact tip assemblies 90a,b,c,d (FIGS. 7b,c,d,e, respectively) to facilitate directed flow of heated fluid to target tissue in the surgical site and to provide the surgeon/operator with tactile feedback when the assembly is placed into contact with target tissue. The tissue contact tip assemblies 90a,b,c,d each include a hub 92 adapted to hold one of a set of tissue contact tips. The hub 92, which is preferably an annular enclosure, may be removably attached to the hot fluid port 44 of the cannula 14 through any known fluidly secure attachment mechanism, such as the threaded connection 94 depicted in the drawings.

FIGS. 7a,b show a tissue contact tip assembly 90a having a roller ball tip 95 rotatably disposed within the hub 92. The roller ball tip 95 may be formed of a porous or a non-porous material. A tip fluid port 96, such as the arcuate channel defined between the tissue contact tip 95 and the hub 92, is provided to permit the flow of heated fluid around and past the tissue contact tip to the tissue in the surgical site. It should be appreciated that the flow of heated fluid about the roller ball tip 95 also acts as a lubricant therefor. The substantially free rolling action of the roller ball tip 95 over target tissue provides reduced friction, enhanced fluid flow directly to the tissue, and permits a tamponade effect on the tissue. Also, it has been found that, due to the contact of the roller ball tip 95 with the target tissue, very low flow rates can be utilized to heat tissue to the desired temperature.

While the roller ball tip 95 is preferred, the tissue contact tip assembly may alternatively employ tips of various geometries including a flat tip 97 (FIG. 7c) or an orbital tip 99 (FIG. 7d), each of which also supply heated fluid through a tip fluid port 96. These tissue contact tips, however, do not roll freely within their respective hubs as does the roller ball tip 95. Rather, they may be stationary or rotate axially within their hubs. Additionally, the tissue contact tip assembly may employ a perforated tissue contact tip 100 (FIG. 7e) to provide multiple fluid ports 101 in addition to or in lieu of tip fluid port 96. Although the drawings show the tissue contact tip as a separate element engaged in its associated hub, it should be understood that the tissue contact tip and hub may be provided as an integral component.

Figure 8A:
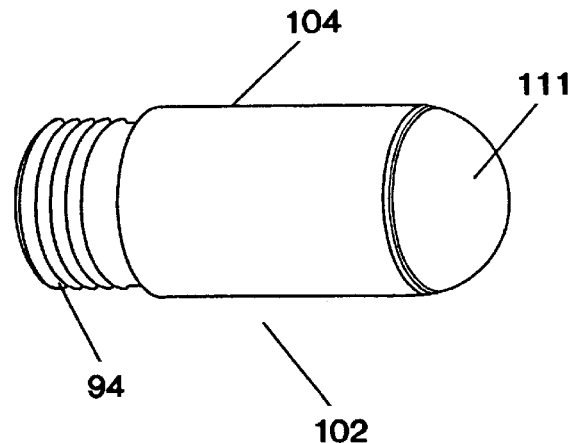
FIG. 8a is an isometric view of an alternative tissue contact tip assembly.
Figure 8B:
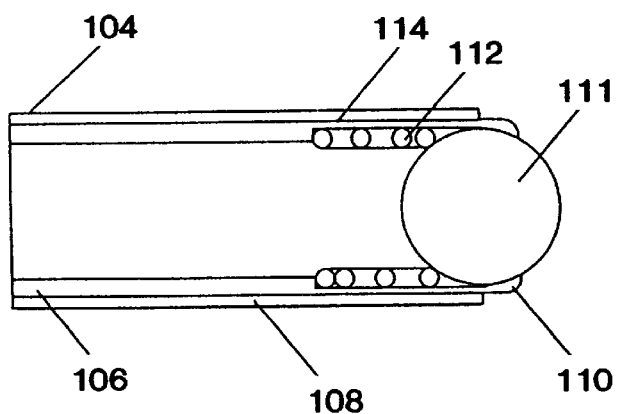

FIGS. 8a,b show an alternative tissue contact tip assembly 102 adapted to function as a valve to control the flow of fluid exiting the hot fluid channel 38 (at the hot fluid port 44) upon contact with tissue in the surgical site. The contact tip assembly 102 preferably includes an elongated hub 104 (FIG. 8a) having an inner wall 106 (FIG. 8b) disposed along the inside surface 108 of the hub. A portion 110 of the inner wall 106 extends beyond the hub 104 and is shaped to seat a contact tip 111, desirably a roller ball tip. The wall portion (or seat) 110 is spring-biased against the contact tip 111 by a resilient biasing member 112 (e.g., a coil spring) in contact with the tip. Preferably, both the biasing member 112 and the contact tip 111 are positioned in a recess 114 defined in the inner wall 106. In this arrangement, the contact tip 111 functions as a valve biased in closed position to block fluid exiting the hot fluid channel 38 from flowing into the surgical site when the tip is not in contact with tissue. Compression of the contact tip 111 against tissue in the surgical site forces the tip into the hub 104 and opens a fluid flow path into the surgical site. It should be appreciated that the flow rate of the fluid exiting the contact tip assembly 102 depends upon the extent to which the contact tip 111 is compressed against the tissue. As with the contact tip assemblies 90a,b,c,d, the contact tip assembly 102 provides tactile feedback to the surgeon/operator when placed into contact with tissue.

Figure 8C:
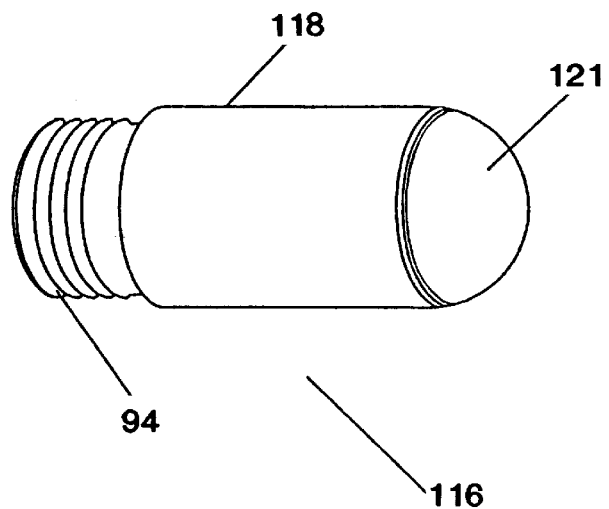
FIG. 8c is an isometric view of yet another alternative tissue contact tip assembly.
Figure 8D:
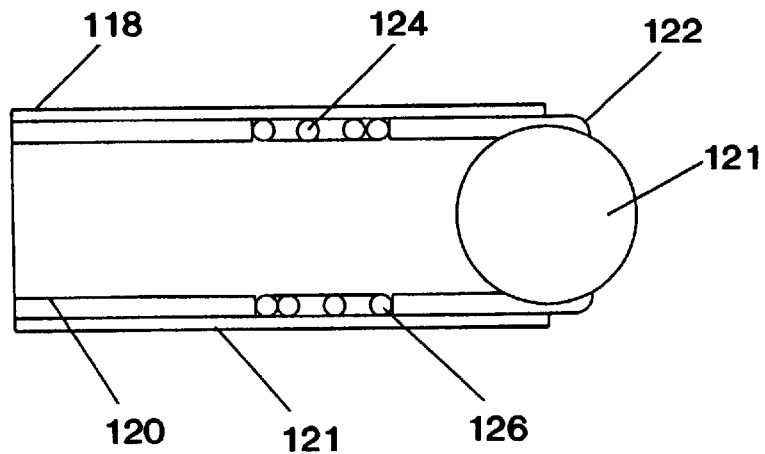
FIG. 8d is a cross-sectional view of the alternative tissue contact tip assembly of FIG. 8c.

FIGS. 8c,d show another alternative tissue contact tip assembly 116 comprising an elongated hub 118 having an inner wall 120 disposed along the inside surface 121 of the hub. A portion 122 of the inner wall 120 extends beyond the hub 118 and is shaped to seat a contact tip 121, preferably a roller ball tip. The wall portion (or seat) 122 is spring-biased against the contact tip 121 by a resilient biasing member 124. The biasing member 124 is positioned in the hub 118 a distance from the tip within a recess 126 defined in the inner wall 120 (unlike the embodiment shown in FIGS. 8a,b, where the biasing member 112 is in contact with the tip 121). It should be understood that, in this arrangement, the contact tip 121 does not act as a valve. Because compression of the contact tip 121 against tissue in the surgical site forces both the tip and the wall portion 122 into the hub 118, a fluid flow path is not altered. A fluid flow path for the contact tip assembly 116 is preferably provided through the contact tip 121 itself (e.g., through one or more perforations therein, or through gaps defined between the contact tip and the wall portion 122, or by selecting a tip formed of a sufficiently porous material). Those skilled in the art will appreciate that the contact tip assembly 116 enables the surgeon/operator to apply a constant compression force on tissue in the surgical site.

Due to their small masses, the described tissue contact tip assemblies rapidly reach temperature equilibrium with the fluid. The tissue contact tip assemblies are particularly useful in areas in which contact with tissue is desirable, such as where there is active bleeding, strictures, tissue bridges, or where mechanical force in addition to heat is desired or required.

DESCRIPTION OF APPLICATIONS

Applications for heated fluid therapy are numerous and include sinonasal surgery, head and neck surgery (otolaryngology), oral surgery, bronchoscopic and tracheal-bronchic surgery, cystoscopic surgery, gastroscopic surgery, and cosmetic surgery (including wrinkle reduction and liposuction). Difficult to access procedures or those carried out near vital structures will particularly benefit from the present invention.

An example of where the present invention has significant utility is in the treatment of sinonasal polyposis. Mechanical and laser surgical management have been known to cause serious complications including blindness, cerebrospinal fluid leak, or subarachnoid hemorrhage. Sharp instruments introduced into the nasal and sinus passages may cause bleeding that impairs the surgeon's visualization of the surgical site and contributes to the incidence of complications. Lasers have also been known to cause cerebrospinal fluid leaks and blindness due to scatter and direct line-of-sight effects.

It should be appreciated that the present invention reduces or eliminates the need for sharp instruments and has no light energy to scatter. The fluid temperature and flow rate are controlled such that the polypoid mass is weakened and can be aspirated out of the patient's body. The benefit of the flowing fluid is that it can reach all of the diseased tissue. Heated saline in the range of 60° C. to 80° C. has been demonstrated to be effective in the treatment of nasal sinus polyposis. Flowing hot fluid is not limited in its ability to reach specific target tissue as are the known expandable balloon-type instruments. Flowing hot fluid also does not work solely in a straight line as does a surgical laser beam.

Within the nasal cavity warm fluid causes mucosal vasoconstriction. This permits surgery with minimal or no vasoconstricting agents such as cocaine. Following irrigation to create the vasoconstriction, the temperature can be increased to 75° C. to 95° C. to treat an enlarged turbinate. The hot fluid tissue contact tip can be used to shrink and coagulate the mass. It should be noted that surgery is a very personal and technique-sensitive art. As such, some surgeons may, and some do, prefer to use lower temperatures (50° C. to 65° C.) for longer exposures to achieve a similar result.

Figure 9:
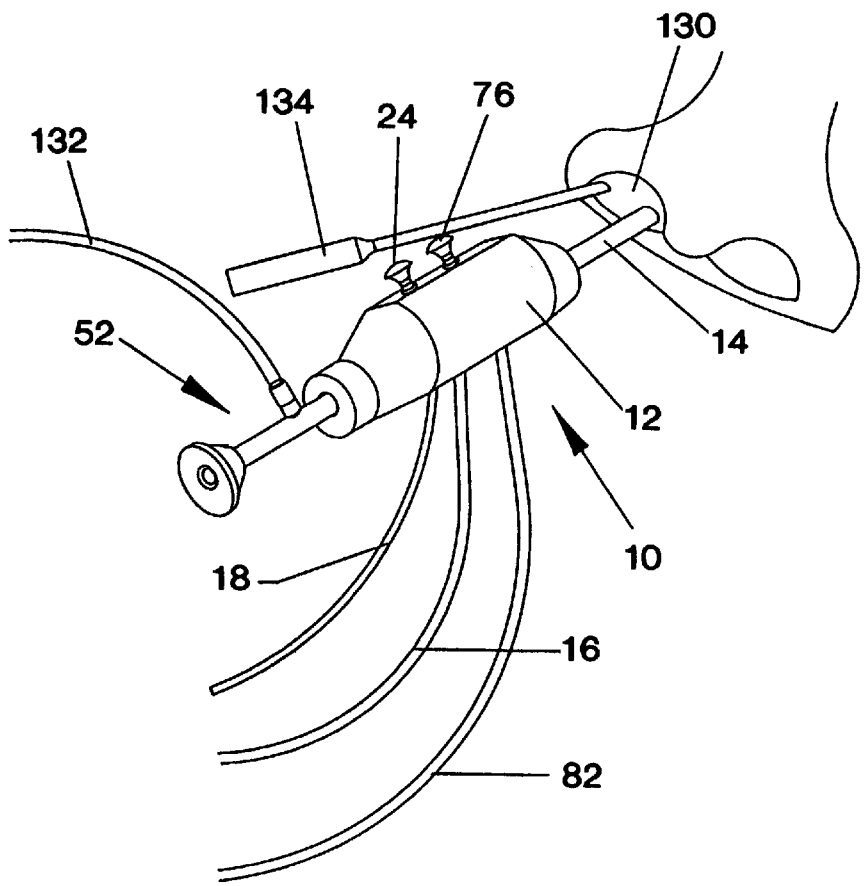
FIG. 9 illustrates the surgical instrument of FIG. 4 in operation during treatment of a sinus-nasal disorder.

FIG. 9 illustrates a sinonasal procedure such as thermal fluid ablation and aspiration of frontal sinus polyps. The heated fluid surgical instrument 10, shown inserted into a nasal opening 130, includes the handpiece 12 including the irrigation and aspiration valve assemblies 24 and 76, the cannula 14, the telescope 52 (provided with a light pipe 132 to illuminate the surgical field), and an accessory instrument 134 for gently grasping and manipulating tissue as required.

Another example of where the present invention is of significant benefit is in the treatment of bullous emphysema. A bullae is a large blister-like structure within the superficial layers of tissue in the lung. In this disease the lung is uncharacteristically enlarged and overdistended. The bullae and blebs (large flaccid vesicles) take up space such that effective lung volume is reduced. This disease is sometimes referred to as "vanishing lung" because the patient has significantly reduced alveolar membrane area for gas exchange to take place. The lung volume per breath (tidal volume) is diminished, while the volume of air remaining in the lung (residual volume) is increased. Simply put, the patient is suffocating.

Treatments for this disorder range from lung transplant to surgical removal of the bullae. These open procedures are now being replaced by a thoracoscopic approach to reduce the lung volume. Lung volume reduction provides healthy lung enough room to expand and exchange gases. In this treatment, both normal and diseased lung tissue are stapled and removed to permit recruitment of a volume of healthy cells. After the staple is placed, lung tissue distal to the staple is excised. However, mechanical techniques using staples are indiscriminate. They necessarily remove healthy tissue along with the diseased tissue. In some cases, access to the diseased portion of the lung is made difficult or impossible. Additionally, this procedure frequently results in air leaks hours or days following surgery.

Lasers are now being used experimentally to reduce lung volume. They attempt to shrink the bullae by heating the tissue. However, since this disease is primarily a result of smoking, the lung tissue has non-uniform absorption due to black deposits of carbon. This results is a very high incidence of laser induced perforation. Even attempts at using absorbing contact probes results in perforation.

The present invention offers a solution to these limitations. Through one or more small (2 mm to 10 mm) incisions to gain access to the lung, the cannula 14 of the handpiece 12 may be inserted through the chest wall. A very slow fluid flow, ranging from around 2 to 50 ml/min of saline, can be used at a temperature ranging from approximately 70° C. to 85° C., depending upon surgical technique and tissue pathology. Tissue shrinkage will occur rapidly. Thus, the surgeon can control the flow and temperature parameters simply by observing the lung volume reduction. Since there are no sharp objects used near the lung, and since the fluid cannot cause vaporization, there is little risk of perforation. Also, the cannula 14 is small enough to be positioned virtually anywhere in the chest cavity. Thus, there is a better opportunity to effectively treat only diseased tissue.

Figure 10:
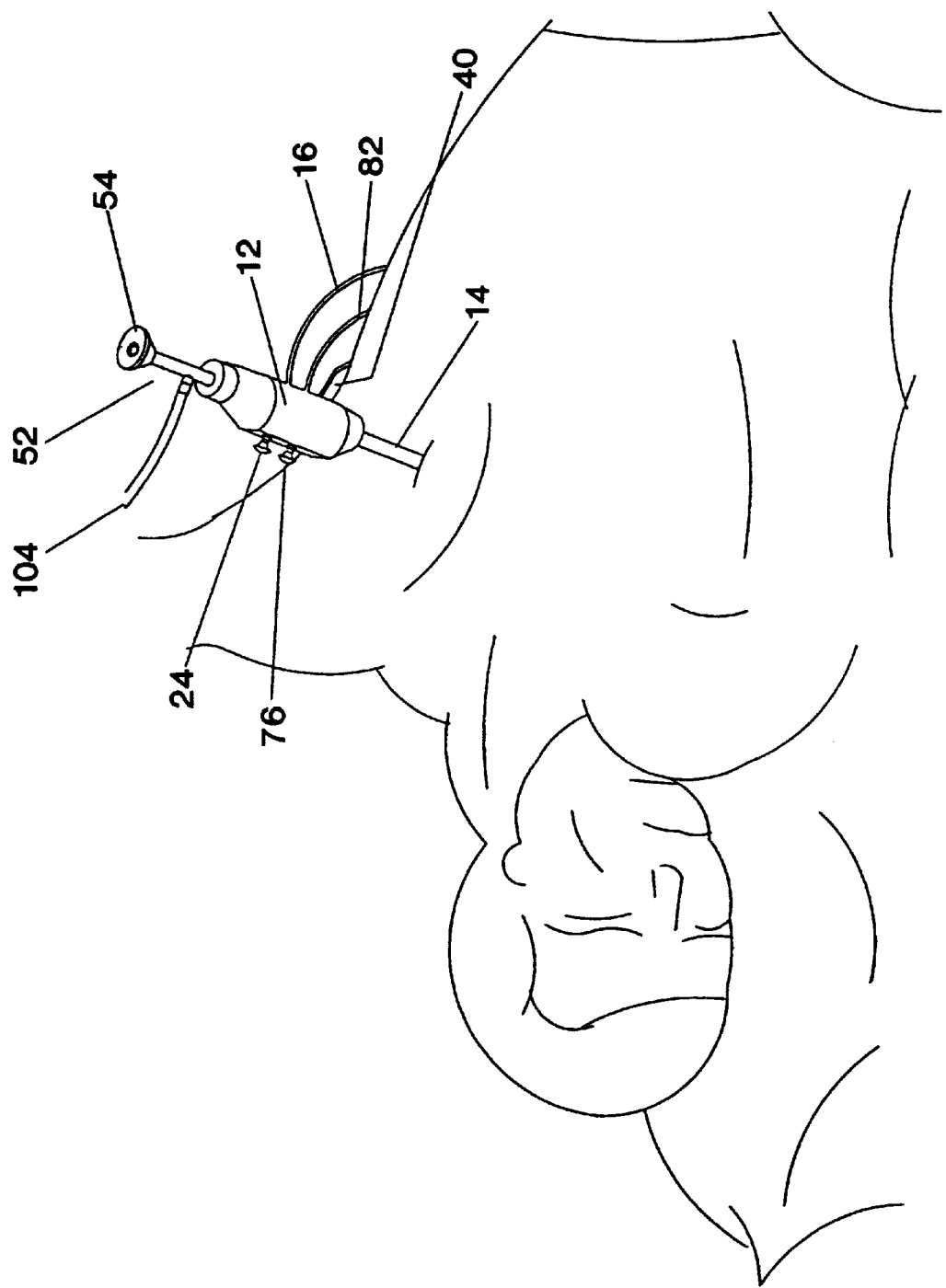
FIG. 10 illustrates the surgical instrument of FIG. 4 in operation during treatment for bullous emphysema.

FIG. 10 illustrates the handpiece 12 fitted with the irrigation valve assembly 24 and the aspiration valve assembly 76 used in the treatment of bullous emphysema with the patient lying in lateral decubitus position (with his/her healthy side down). A surgical incision in the patient's chest provides access for the cannula 14 through which the telescope 52 and/or other surgical instruments may be inserted. Flow and temperature control are managed through the valve assemblies 24 and 76.

In sum, it will be understood by those skilled in the medical arts that the controlled use of the heated fluid surgical instrument 10 will permit one or more of the following clinical end-points to be achieved:

Vasoconstriction: under elevated temperature irrigation in the range of approximately 39° C. to 41° C., mucosal vasoconstriction can result. Under conditions of thermo-vasoconstriction, mechanical manipulation and limited incisional procedures can be performed in a hemostatic field. This has the benefit of reducing blood loss and improving the surgeon's field of view. This combination of effects makes the surgical procedure safer, faster, and easier to perform. In certain cases (e.g., sinonasal polyposis), no vasoconstricting agents such as cocaine are required.

Superficial coagulation: Elevating the fluid temperatures in the range of approximately 45° C. to 95° C., the tissue is weakened as a result of the thermal denaturation of protein. It has been observed that diseased tissue will blanch and be mechanically weakened faster and at lower temperatures than healthy tissue. Thus, in certain instances, diseased tissue can be easily removed without disruption of surrounding normal tissue or the need for sharp instruments. However, if mechanical instruments are used, they will be able to remove the tissue faster and easier. In certain instance (e.g., removal of polyps within the nasal sinuses), the tissue may simply be aspirated out of the body without use of any mechanical instruments. This affords a very safe and complete removal of diseased tissue.

Other tissues will shrink or cause reduction in tissue volume as a result of thermal coagulation caused by fluids in this temperature range. The shrinkage can have a significant clinical benefit. For example, following endoscopic access to the lung, heated fluid therapy in the range of 70° C. to around 85° C., depending upon surgical technique, pathology, etc., will reduce the lung volume as an effective treatment of bullous emphysema. The benefit of this application of heated fluid is a lung reduction procedure without the risk of perforation common with lasers and mechanical lung reduction techniques.

Full thickness coagulation and ablation: Longer duration, elevated temperature exposure can cause deeper tissue thermal coagulation. This dose related response will bring about necrosis in tissue that can be surgically removed at the time of surgery or permitted to slough or be re-absorbed by the body over time. This therapy can be effective for destruction of small to medium sized solid tumors or lesions.

While the present invention has been disclosed in illustrative form, and particularly in detail for sinonasal and thoracic applications, it will be apparent to those skilled in the art that numerous modifications, variations, and/or other changes may be made to this invention. For example, it may be possible to use a pre-heater to warm the input fluid tube or use a valve other that a manual trumpet valve to control fluid flow rate and temperature. Accordingly, reference should be made to the appended claims, rather than to the foregoing specification, as indicating the scope of the invention.

What is claimed is:

1. A surgical apparatus for heating a localized area of tissue within a patient's body comprising:

a handpiece adapted to receive a fluid under pressure;

a fluid reservoir defined within the handpiece;

a heater housed in the handpiece for heating fluid in the fluid reservoir;

a cannula attached to an end of the handpiece and extending therefrom for insertion into the patient's body, the cannula including a hot fluid channel; and an irrigation control valve assembly operatively associated with the handpiece for directing the flow of fluid through the heated fluid reservoir in the handpiece and into and through the hot fluid channel of the cannula.

2. A surgical apparatus for heating a localized area of tissue within a patient's body comprising:

a handpiece adapted to receive a fluid under pressure;

a fluid reservoir defined within the handpiece;

a heater housed in the handpiece for heating fluid in the fluid reservoir;

a cannula attached to an end of the handpiece and extending therefrom for insertion into the patient's body, the cannula including an outer sleeve surrounding a hot fluid channel and an irrigation channel; and an irrigation control valve assembly operatively associated with the handpiece for selectably directing the flow of fluid through the handpiece into at least one of a first and a second fluid flow path, the first flow path bypassing the fluid reservoir and passing fluid into and through the irrigation channel of the cannula, the second flow path passing fluid through the fluid reservoir and into and through the hot fluid channel of the cannula.

3. A surgical apparatus as in claim 2, further comprising a temperature sensor disposed in a fluid flow path for sensing the temperature of the fluid, and a temperature controller operatively linked to the sensor and to the heater for supplying power to the heater and for selectably controlling the temperature of the fluid in the flow path in response to input signals received from the sensor.

4. A surgical apparatus as in claim 2, wherein the handpiece is insulated.

5. A surgical apparatus as in claim 2, further comprising a tissue contact tip assembly at a distal end of the hot fluid channel of the cannula for contacting a localized area of tissue and providing tactile feedback to an operator, the tissue contact tip assembly being adapted to pass fluid exiting the hot fluid channel into the patient's body.

6. A surgical apparatus as in claim 5, wherein the tissue contact tip assembly includes a contact tip seated in a seat, the seat being biased against the contact tip.

7. A surgical apparatus as in claim 6, wherein the contact tip operates as a valve for controlling fluid flow exiting the hot fluid channel upon contact with the localized area of tissue.

8. A surgical apparatus as in claim 5, wherein the tissue contact tip assembly includes a roller ball tip disposed therein so as to permit substantially free rotation of the tip as it travels over the localized area of tissue.

9. A surgical apparatus as in claim 5, wherein the tissue contact tip assembly includes a flat tip.

10. A surgical apparatus as in claim 5, wherein the tissue contact tip assembly includes a tissue contact tip having a plurality of perforations defining fluid ports.

11. A method for heating a localized area of tissue in a patient's body comprising the steps of:

inserting a handpiece having a cannula operatively attached thereto into the localized area of tissue;

delivering a physiologically compatible fluid into the handpiece;

adjusting an irrigation control valve assembly operatively associated with the handpiece to direct the flow of the fluid through a fluid reservoir heated by a heater in the handpiece, into and through a hot fluid channel in the cannula, and out a tissue contact tip assembly disposed at a distal end of the hot fluid channel of the cannula; and placing the tissue contact tip assembly into contact with the localized area of tissue.

12. A method according to claim 11 for treating bullous emphysema, wherein the localized area of tissue includes emphysematous bullae.

13. A method according to claim 11 for treating sinus polyposis wherein the localized area of tissue includes mucosa and polyp.

14. A method for heating a localized area of tissue in a patient's body comprising the steps of:

inserting a handpiece having a cannula operatively attached thereto into the localized area of tissue;

delivering a physiologically compatible fluid into the handpiece; and adjusting an irrigation control valve assembly operatively associated with the handpiece to direct the flow of fluid into at least one of a first and a second fluid flow path through the handpiece, fluid in the first flow path passing into and through an irrigation channel in the cannula bypassing a fluid reservoir heated by a heater in the handpiece, fluid in the second flow path passing through the heated fluid reservoir in the handpiece and into and through a hot fluid channel in the cannula.

15. A method according to claim 14 for treating bullous emphysema, wherein the localized area of tissue includes emphysematous bullae.

16. A method according to claim 14 for treating sinus polyposis wherein the localized area of tissue includes mucosa and polyp.

* * * * *